United States Patent
Radziwon et al.

(10) Patent No.: US 6,726,321 B2
(45) Date of Patent: Apr. 27, 2004

(54) SIDE SHIELD RETENTION CLAMP

(75) Inventors: Norman J. Radziwon, Rochester, NY (US); Nicola S. Verdino, Rochester, NY (US)

(73) Assignee: ArtCraft New York, Rochester, NY (US)

(*) Notice: Subject to any disclaimer, the term of this patent is extended or adjusted under 35 U.S.C. 154(b) by 102 days.

(21) Appl. No.: 10/143,708

(22) Filed: May 10, 2002

(65) Prior Publication Data
US 2003/0208826 A1 Nov. 13, 2003

(51) Int. Cl.[7] .................................................. G02C 5/00
(52) U.S. Cl. ..................... 351/140; 351/44; 351/121; 2/450
(58) Field of Search ........................... 351/44, 111, 119, 351/121, 140, 141; 2/448, 449, 450

(56) References Cited

U.S. PATENT DOCUMENTS

| | | | |
|---|---|---|---|
| 4,703,522 A | * 11/1987 | Schurle et al. .................. | 2/432 |
| 4,785,481 A | * 11/1988 | Palmer et al. .................. | 2/436 |
| 5,548,351 A | 8/1996 | Hirschman et al. ............ | 351/47 |
| 5,748,278 A | 5/1998 | Simmons, Sr. ................. | 351/44 |
| 5,798,815 A | 8/1998 | Hirschman et al. ............ | 351/44 |
| 5,940,161 A | * 8/1999 | Hirschman et al. ............ | 351/44 |
| 6,007,196 A | 12/1999 | Saba et al. ..................... | 351/44 |
| 6,270,216 B1 | * 8/2001 | DiChiara ....................... | 351/44 |

* cited by examiner

Primary Examiner—Huy Mai
(74) Attorney, Agent, or Firm—Brown & Michales, PC

(57) ABSTRACT

This side shield retention clamp for locking an eyeglass side shield having a side hole to a temple of an eyeglass frame has a temple clamp with an arm extending therefrom having a hole rather than a hook at its end. A screw extends through the hole, but is not tapped into the hole. Instead, a threaded shield clamping nut extends into the hole in the side shield from the inside of the shield. This screw is threaded through this shield clamping nut and contacts the temple. In contrast to this, the screw tightening the temple clamp engages the clamp directly rather than pressing against the temple. In the preferred embodiment, the shield clamping nut has a projection with a flat face that fits against the outside of the temple, extends into the clamp slot, and is clamped against the temple when the clamp is tightened (via a clamp screw).

20 Claims, 6 Drawing Sheets

SIDE SHIELD RETENTION CLAMP

TECHNICAL FIELD

This invention deals with a side shield retention clamp for eyeglasses.

BACKGROUND OF THE INVENTION

Side shields can be mounted to the temples of safety eyeglass frames to help shield the wearer from dangerous materials that could enter the eye in a particular work environment. In fact, employers often provide employees working in such environments with their own personal prescription eyeglasses having side shields at no cost in order to safeguard their workers' health and productivity. Unfortunately, many workers are tempted to remove the side shields when not in the workplace in order to make their eyeglasses appear more stylish or appealing. This leads to the loss of the side shields provided and often leads to the worker attempting jobs where safety requires the presence of such side shields without the shields being present.

In order to prevent the removal and loss of side shields, employers and manufacturing facilities have sought means for permanently affixing side shields to the temples of the eyeglasses provided to their employees. Mechanical locking means (such as rivets, screws, and lock nuts) as well as adhesives have been used for this purpose. Representative examples of prior art attempts to solve this problem using mechanical locking means can be seen in the following U.S. patents:

U.S. Pat. No. 5,548,351 issued to Hirschman et al. in 1996 for a "Method and Kit for Attaching Side Shields to Eyeglass Temples."

U.S. Pat. No. 5,748,278 issued to Simmons, Sr. in 1998 for a "Eyeglass Shield for Removable Attachment to Eyeglass Lens Frames."

U.S. Pat. No. 5,798,815 issued to Hirschman et al. in 1998 for a "Method and Kit for Attaching Side Shields to Eyeglass Temples."

U.S. Pat. No. 6,007,196 issued to Saba et al. in 1999 for a "Retainer for Eyeglass Frames having Sideshields."

Most of the foregoing patents deal with systems that require a specialized eyeglass shield for their use. Saba et al. describe an eyeglass shield attachment mechanism that is intended for use with a common slide-on shield. Such shields are placed in position by sliding them into place on the temple adjacent the lens frame. They can be removed by reversing this process and sliding them back from their position. They can also be removed by separating the temple from the eyeglass frame and sliding the shield forward. Thus, some mechanism must be provided to block them from sliding forward or back from the end of the temple adjacent the lens frame. Saba et al. provide a hook with a lip that fastens into an appropriately shaped side opening in the eyeglass shield. This hook is at one end of an arm with the other end attached to a clamp that can be tightened onto the temple behind the shield after the shield is in position. While this method can provide some benefits, it is far from perfect. For example, the apparatus of Saba et al. is subject to easy removal by rotating the side shield around the axis formed by the temple of the glasses—i.e.—it remains easy to remove by twisting. Thus, there remains a need for efficient and effective mechanical means for securely affixing common slide-on side shields to the temples of eyeglasses.

SUMMARY OF THE INVENTION

Overall, my invention can be summarized as a temple clamp having an arm extending therefrom with a hole rather than a hook at the end of this arm. A screw extends through the hole, but is not tapped into the hole. Instead, in my preferred embodiments, I use a sliding fastener comprised of a shield clamping nut arranged on a projection that extends along an outside face of the temple. The nut extends into a hole in the side shield from the inside of the shield and has interior threads. The screw is threaded through these to be jammed against the temple. The projection has a flat face that fits against the outside of the temple, extends into the clamp slot, and is clamped against the temple when the clamp is tightened (via a clamp screw). Only the screw projecting through the shield clamping nut against the temple engages the temple, as the clamp screw passes under the temple and engages the opposing side of the clamp directly. Thus, my invention uses an arm attached to a clamp to hold a screw that receives a nut to hold a side shield in position. In the preferred embodiment, both the screw and the nut extend through the side shield. The nut and its projection are on the inside of the shield and the arm from the clamp is on the outside of the shield so that these parts straddle the shield, with at least a portion of the nut extending into the hole in the side shield.

This arrangement provides a strong and non-twistable clamp firmly engaging both sides of the temple and also a strong engagement with the shield by disposing a nut and screw that extend directly through a hole in the shield and are also clamped to the temple. The result is generally more complex than prior art devices since two screws are involved, but it is also much more secure than these devices.

DESCRIPTION OF THE INVENTION

Figure 1A:
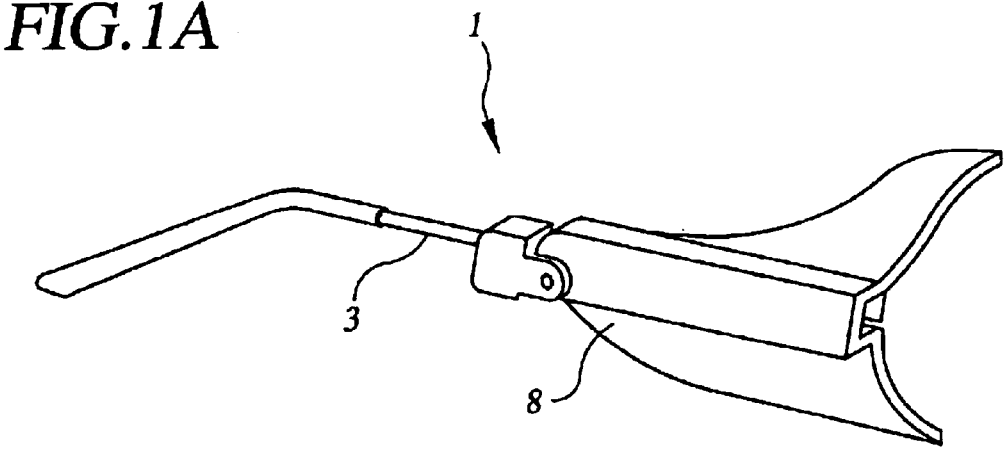
FIG. 1A provides a perspective view from the outside of my invention holding a side shield in place on an eye glass temple.
Figure 1B:
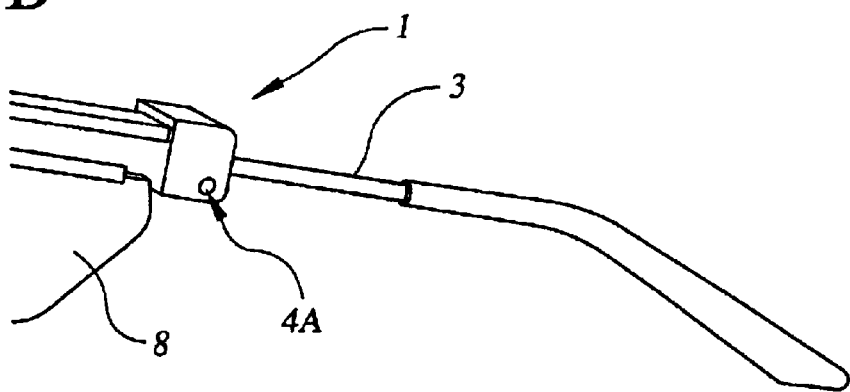
FIG. 1B provides a perspective view from the inside of my invention holding a side shield in place on an eye glass temple.
Figure 1C:
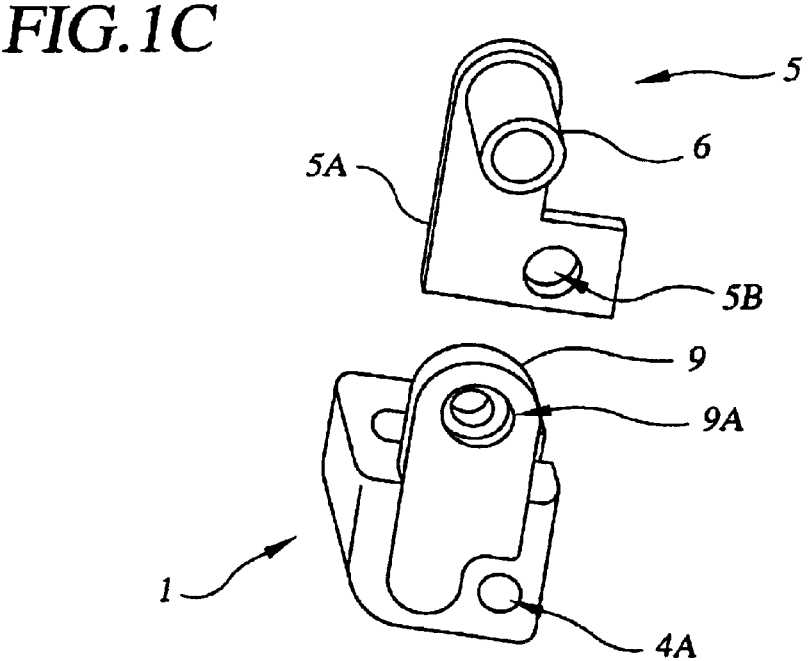
FIG. 1C provides an exploded perspective view showing the principal parts making up of the side shield retention clamp of my invention.
Figure 1D:
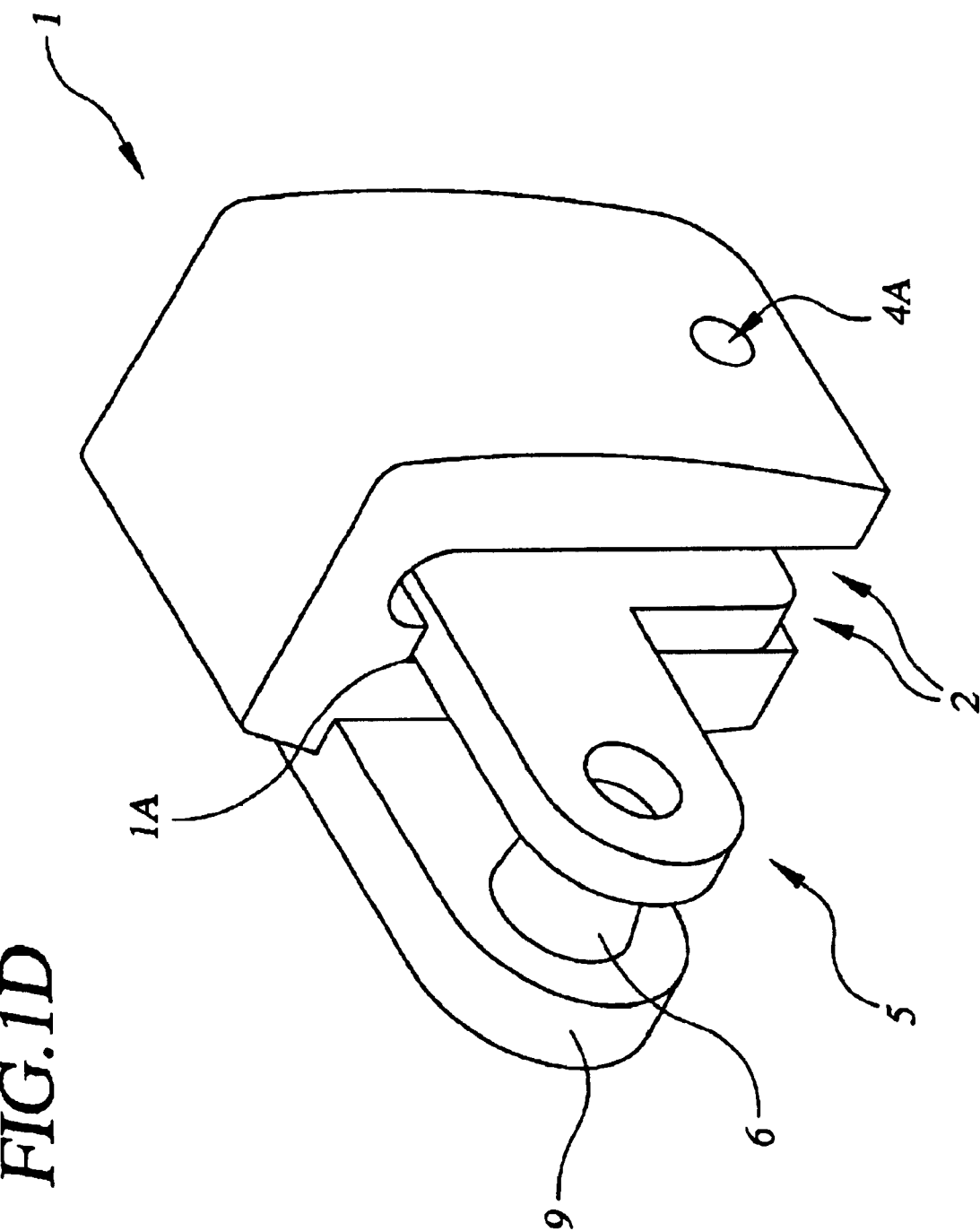
FIG. 1D provides a first perspective view of the side shield retention clamp of my invention with its principal parts in place.
Figure 2:
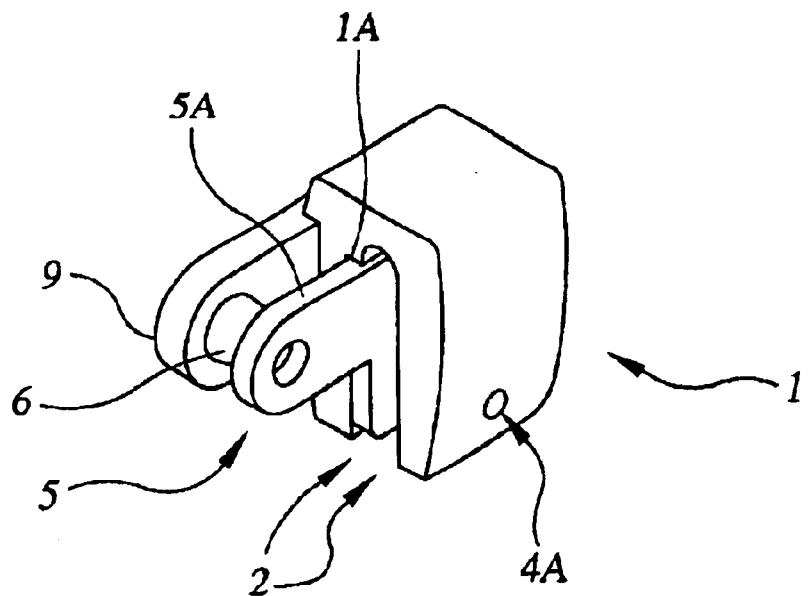
FIG. 2 provides a second perspective view of the side shield retention clamp of my invention with its principal parts in place.
Figure 3:
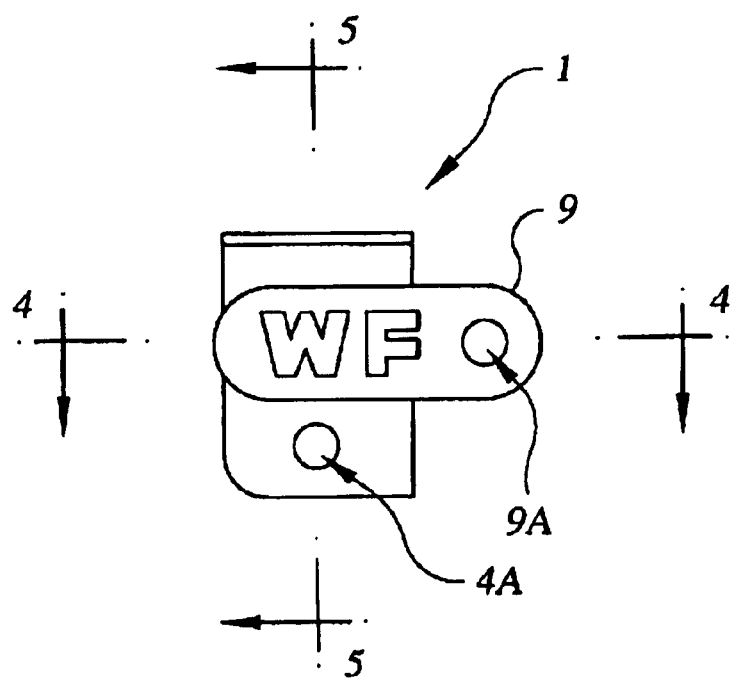
FIG. 3 provides a side view of the side shield retention clamp of my invention.
Figure 4:
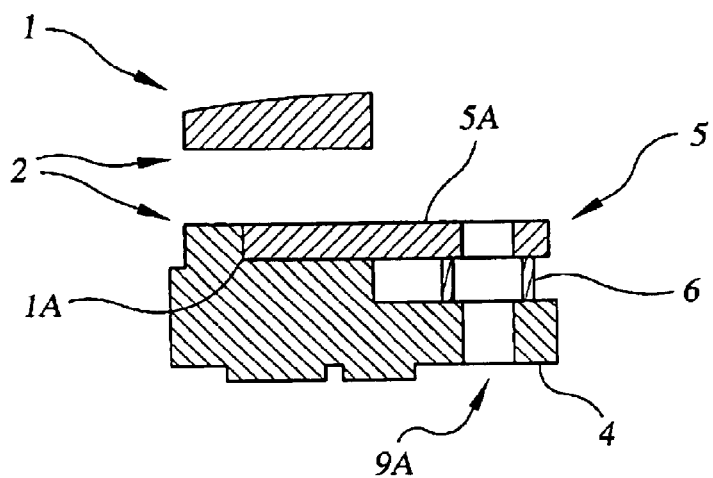
FIG. 4 provides a cross-sectional view taken through line 4—4 of FIG. 3.
Figure 5:
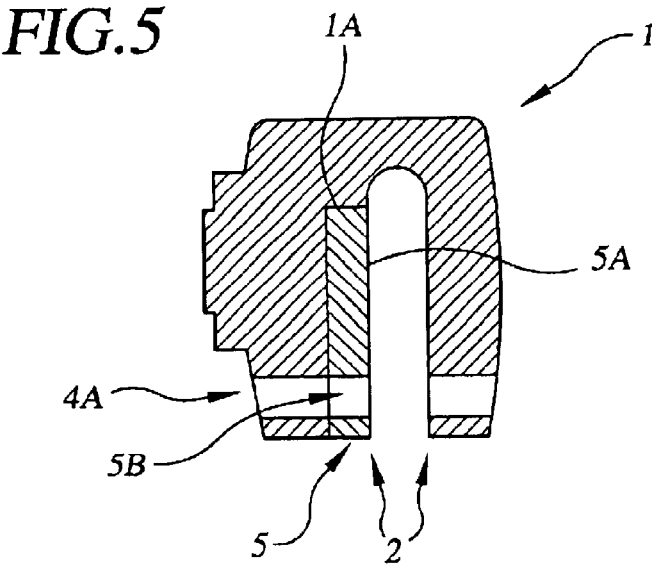
FIG. 5 provides a cross-sectional view taken through line 5—5 of FIG. 3.
Figure 6:
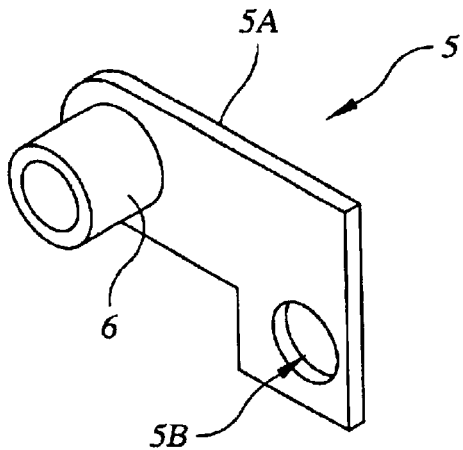
FIG. 6 provides a perspective schematic view of the sliding fastener of my invention.
Figure 7:
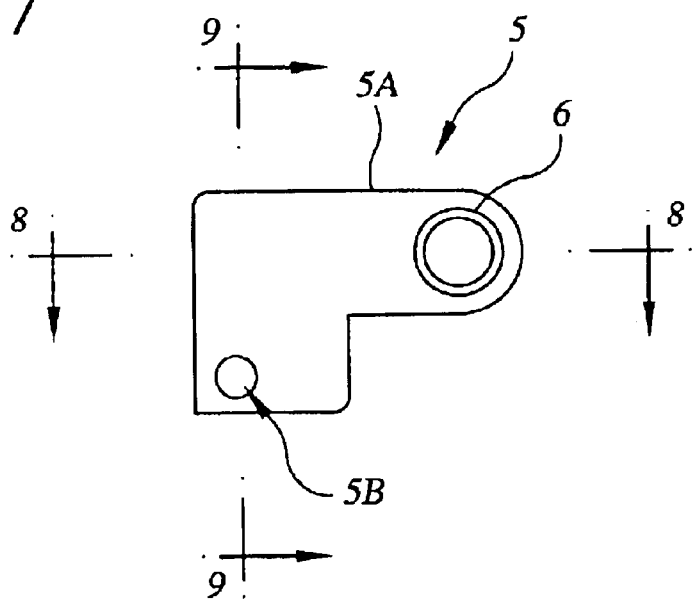
FIG. 7 provides a side view of the sliding fastener of my invention.
Figure 8:
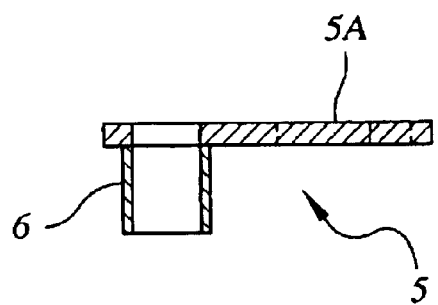
FIG. 8 provides a cross-sectional view taken through line 8—8 of FIG. 7.
Figure 9:
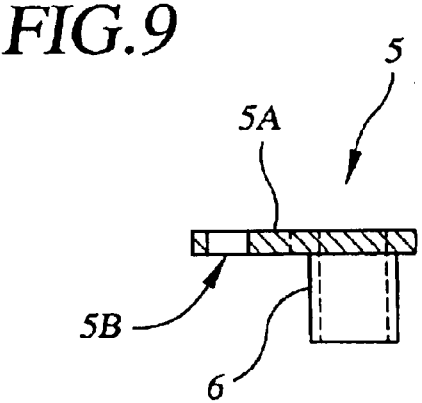
FIG. 9 provides a cross-sectional view taken through line 9—9 of FIG. 7.
Figure 10:
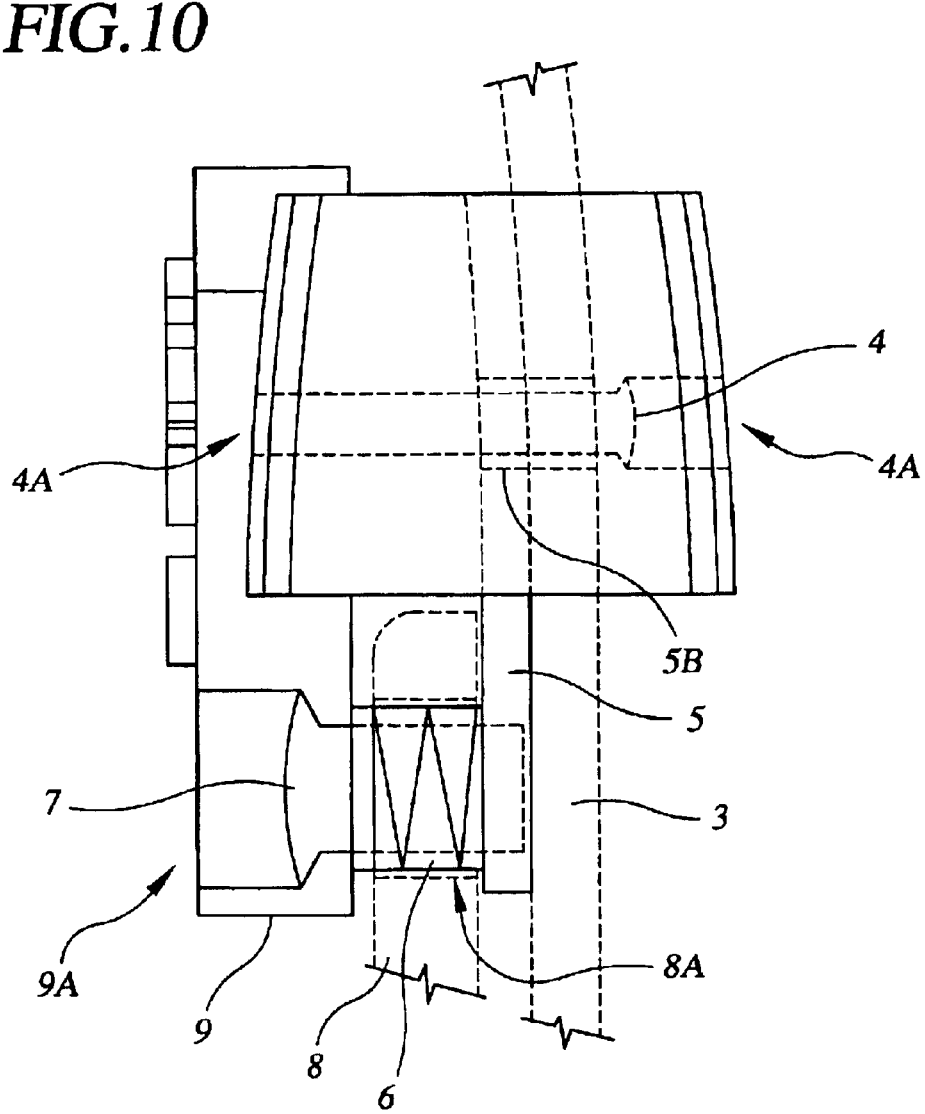
FIG. 10 provides a cross-sectional schematic view of my invention holding a side shield firmly in place on an eyeglass temple.
Figure 11:
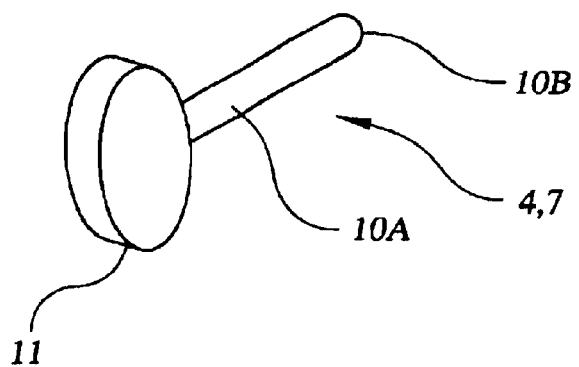
FIG. 11 provides a perspective view of a break away screw suitable for use with this invention.

My invention uses an improved temple clamp (denoted generally by arrow 1) that clamps the opposed interior faces (denoted generally by arrows 2) of its two sides against an eyeglass temple 3 with a temple clamping screw 4 inserted in a temple clamping screw hole 4A. Temple clamping screw 4 draws the opposing faces 2 of the two opposing sides of temple clamp 1 tight against temple 3, rather than driving in against temple 3 itself like a set screw.

The foregoing arrangement provides a sturdier clamp that is less resistant to being twisted off the temple. Applying a clamp with a set screw, as is done in prior art, leaves one face of the clamp against the temple and a set screw jammed against the opposite side of the temple. This creates a type of three-point contact, allowing the clamp to be rolled off the temple by twisting.

The preferred embodiments of my invention illustrated use a sliding fastener (denoted generally as 5) incorporating a shield clamping nut 6 in conjunction with a shield clamping screw 7 to securely fasten the side shield 8 to an arm 9 extending from temple clamp 1. The shield clamping screw 7 also penetrates through shield clamping nut 6 to press up against the temple 3 of the eyeglasses used, serving to further secure my device in position.

Thus, my invention can be summarized as a temple clamp 1 having an arm 9 extending therefrom with a hole 9A. A shield clamping screw 7 is placed through hole 9A, but is not tapped into hole 9A. Instead, I use a sliding fastener 5 featuring a clamping nut 6 arranged on a projection 5A that extends along an outside face of temple 3. Shield clamping nut 6 extends into a hole 8A in the side shield 8 from the inside. Shield clamping nut 6 has interior threads and shield clamping screw 7 is threaded through these to be jammed against temple 3. As shield clamping nut 6 presses against temple 8, it causes it to bind even more tightly against the opposed surfaces 2 of temple clamp 1, further securing it to this member.

Projection 5A has a flat face that fits against the outside of temple 3 and extends into temple clamp 1 where a special cut-out slot 1A can be provided for it. Projection 5A is clamped against temple 3 within temple clamp 1 when temple clamp 1 is tightened via temple clamping screw 4. In the preferred embodiment illustrated, the lower portion of projection 5A extends across temple clamping screw hole 4A. Thus, it is provided with an extension hole 5B that is penetrated by temple clamping screw 4 when this screw is placed in position. These features make sliding fastener 5 into a virtual second arm of temple clamp 1, further securing the connection between temple clamp 1 and side shield 8.

Considering the purposes of this invention, it may be advantageous for temple clamping screw 4 and shield clamping screw 7 to be formed with a breakaway section 10A that can break away from the engaged portions 10B of temple clamping screw 4 and shield clamping screw 7 after they have been fully tightened. The breakaway section 10A of screws 4, 7 can be conveniently provided with a perpendicular section that can be used as a handle 11 in manually tightening the aforesaid screws 4, 7.

In the preferred embodiment illustrated, temple clamp 1 and sliding fastener 5 are formed from molded plastic materials. However, metal reinforcing members can be provided within these molded parts if additional strength is desired. Other and additional variations in my invention are possible without exceeding the scope of its underlying inventive concepts. It should, therefore, be understood that my Side Shield Retention Clamp in any of its aspects can be incorporated in many different constructions. Thus, the generality of the claims that follow is not to be superseded by the particularity of the foregoing description or the attached drawings. Many alterations, modifications, and/or additions can be made without exceeding the ambit of the following claims.

We claim:

1. A side shield retention clamp for locking an eyeglass side shield having a side hole to a temple of an eyeglass frame, the side shield retention clamp comprising:
   a temple clamp having two opposing sides;
   a temple clamp screw for tightening the temple clamp extending between the two opposing sides of said temple clamp;
   an arm extending from the temple clamp with a hole in an end of said arm distant from the temple clamp;
   a shield clamping nut; and
   a shield clamping screw that screws into said shield clamping nut, which screw is adapted for placement through said hole.

2. A side shield retention clamp as described in claim 1 where the shield clamping nut has a portion adapted for placement through the side hole of an eyeglass side shield from a side of the side shield adjacent the temple.

3. A side shield retention clamp as described in claim 1 where the shield clamping screw is not tapped into the hole.

4. A side shield retention clamp as described in claim 1 where the shield clamping screw can be tightened so that it extends through the shield clamping nut and contacts the temple of an eyeglass frame to which the side shield is attached.

5. A side shield retention clamp as described in claim 1 where the shield clamping nut has a projection that extends from the shield clamping nut into the temple clamp so that this projection is tightly held by the temple clamp when the temple clamp is tightened.

6. A side shield retention clamp as described in claim 5 where the projection has a flat face that extends along the side of the temple and is pressed against the temple when the temple clamp is tightened.

7. A side shield retention clamp as described in claim 5 where the projection fits into a cut-out in a side of the temple clamp.

8. A side shield retention clamp as described in claim 6 where the projection fits into a cut-out in a side of the temple clamp.

9. A side shield retention clamp for locking an eyeglass side shield having a side hole to a temple of an eyeglass frame, the side shield retention clamp comprising:
   a temple clamp having two opposing sides;
   a temple clamp screw for tightening the temple clamp extending between the two opposing sides of said temple clamp;
   an arm extending from the temple clamp with a hole in an end of said arm distant from the temple clamp;
   a shield clamping nut, which shield clamping nut has a portion adapted for placement through the side hole of an eyeglass side shield from a side of the side shield adjacent the temple; and
   a shield clamping screw that screws into said shield clamping nut, which screw is adapted for placement through said hole and is not tapped into said hole.

10. A side shield retention clamp as described in claim 9 where the shield clamping screw can be tightened so that it extends through the shield clamping nut and contacts the temple of an eyeglass frame to which the side shield is attached.

11. A side shield retention clamp as described in claim 9 where the shield clamping nut has a projection that extends from the shield clamping nut into the temple clamp so that this projection is tightly held by the temple clamp when the temple clamp is tightened.

12. A side shield retention clamp as described in claim 11 where the projection has a flat face that extends along the side of the temple and is pressed against the temple when the temple clamp is tightened.

13. A side shield retention clamp as described in claim 11 where the projection fits into a cut-out in a side of the temple clamp.

14. A side shield retention clamp as described in claim 12 where the projection fits into a cut-out in a side of the temple clamp.

15. A side shield retention clamp for locking an eyeglass side shield having a side hole to a temple of an eyeglass frame, the side shield retention clamp comprising:

a temple clamp having two opposing sides;

a temple clamp screw for tightening the temple clamp extending between the two opposing sides of said temple clamp;

an arm extending from the temple clamp with a hole in an end of said arm distant from the temple clamp;

a shield clamping nut, which shield clamping nut has a portion adapted for placement through the side hole of an eyeglass side shield from a side of the side shield adjacent the temple and a projection that extends from the shield clamping nut into the temple clamp so that this projection is tightly held by the temple clamp when the temple clamp is tightened; and a shield clamping screw that screws into said shield clamping nut, which screw is adapted for placement through said hole and is not tapped into said hole.

16. A side shield retention clamp as described in claim 15 where the shield clamping screw can be tightened so that it extends through the shield clamping nut and contacts the temple of an eyeglass frame to which the side shield is attached.

17. A side shield retention clamp as described in claim 15 where the projection has a flat face that extends along the side of the temple and is pressed against the temple when the temple clamp is tightened.

18. A side shield retention clamp as described in claim 15 where the projection fits into a cut-out in a side of the temple clamp.

19. A side shield retention clamp as described in claim 16 where the projection fits into a cut-out in a side of the temple clamp.

20. A side shield retention clamp as described in claim 17 where the projection fits into a cut-out in a side of the temple clamp.

* * * * *